US012673066B2

(12) United States Patent
Yamamura et al.

(10) Patent No.: US 12,673,066 B2
(45) Date of Patent: Jul. 7, 2026

(54) THERAPEUTIC AGENT FOR PROGRESSIVE DISEASE CAUSED BY INCREASE IN EOMES-POSITIVE CD4-POSITIVE T CELLS

(71) Applicant: National Center of Neurology and Psychiatry, Tokyo (JP)

(72) Inventors: Takashi Yamamura, Kodaira (JP); Shinji Oki, Kodaira (JP); Benjamin Joseph Edward Raveney, Kodaira (JP); Wakiro Sato, Kodaira (JP); Tomoko Okamoto, Kodaira (JP)

(73) Assignee: National Center of Neurology and Psychiatry, Tokyo (JP)

( * ) Notice: Subject to any disclaimer, the term of this patent is extended or adjusted under 35 U.S.C. 154(b) by 544 days.

(21) Appl. No.: 18/034,784

(22) PCT Filed: Nov. 6, 2020

(86) PCT No.: PCT/JP2020/041603
§ 371 (c)(1),
(2) Date: May 1, 2023

(87) PCT Pub. No.: WO2022/097287
PCT Pub. Date: May 12, 2022

(65) Prior Publication Data

US 2023/0405033 A1 Dec. 21, 2023

(51) Int. Cl.
*A61K 31/7028* (2006.01)
*A61P 25/00* (2006.01)
*A61P 43/00* (2006.01)

(52) U.S. Cl.
CPC .......... *A61K 31/7028* (2013.01); *A61P 25/00* (2018.01); *A61P 43/00* (2018.01)

(58) Field of Classification Search
CPC .................................................. A61K 31/7032
See application file for complete search history.

(56) References Cited

U.S. PATENT DOCUMENTS

2017/0151270 A1* 6/2017 Yamamura ................ A61P 1/16

FOREIGN PATENT DOCUMENTS

| | | | |
|---|---|---|---|
| EP | 3144002 | A1 | 3/2017 |
| JP | 2004-501165 | A | 1/2004 |
| WO | 01/98357 | A2 | 12/2001 |
| WO | 03/016326 | A1 | 2/2003 |
| WO | 2016/002827 | A1 | 1/2016 |
| WO | 2016/114386 | A1 | 7/2016 |
| WO | 2018/101261 | A1 | 6/2018 |

OTHER PUBLICATIONS

Ahmadi, A. et al., Health Sci Report, "The role of NK and NKT cells in the pathogenesis and improvement of multiple sclerosis following disease-modifying therapies", 2022, vol. 5, e489 (Year: 2022).*
Chemin, K. et al., Eur. J. Immunol., "EOMES-positive CD4+ T cells are increased in PTPN22 (1858T) risk allele carriers", 2018, vol. 48, pp. 655-669 (Year: 2018).*
Chen, S. et al., CNS Neurosci. Ther., "Eomesodermin expression in CD4+T-cells associated with disease progression in amyotrophic lateral sclerosis", 2024, vol. 30, e14503 (Year: 2024).*
Dhume, K. et al., Biomolecules, "Regulation of CD4 T Cell Responses by the Transcription Factor Eomesodermin", 2022, vol. 12, 1549 (Year: 2022).*
Llao-Cid, L. et al., Leukemia, "EOMES is essential for antitumor activity of CD8+ T cells in chronic lymphocytic leukemia", 2021, vol. 35, pp. 3152-3162 (Year: 2021).*
Prasad, P. et al., Molecular and Cellular Biochemistry, "Rheumatoid arthritis: advances in treatment strategies", 2023, vol. 478, pp. 69-88 (Year: 2023).*
Raveney, B. J. E. et al., PNAS, "Involvement of cytotoxic Eomes-expressing CD4+ T cells in secondary progressive multiple sclerosis", 2021, vol. 118, No. 11, e201818118 (Year: 2021).*
Office Action issued in counterpart Canadian Patent Application No. 3200571 dated Jun. 27, 2025.
International Search Report issued in corresponding International Patent Application No. PCT/JP2020/041603 dated Dec. 28, 2020.
International Preliminary Report on Patentability and Written Opinion issued in corresponding International Patent Application No. PCT/JP2020/041603 dated May 19, 2023.
Pearce et al., "Control of effector CD8+ T cell function by the transcription factor Eomesodermin," Science, 302: 1041-1043 (2003).
Dejean et al., "The role of Eomes in human CD4 T cell differentiation: A question of context," European Journal of Immunology, 49: 38-41 (2019).
Mollo et al., "Virus-specific CD4 and CD8 T cell responses in the absence of Th1-associated transcription factors," Journal of Leukocyte Biology, 95 (5): 705-713 (2014).
Lassmann et al., "Progressive multiple sclerosis: pathology and pathogenesis," Nature Reviews Neurology, 8: 647-656 (2012).
Koch et al., "Treatment trials in progressive MS—current challenges and future directions," Nature Reviews Neurology, 9: 496-503 (2013).

(Continued)

*Primary Examiner* — Bahar Craigo
(74) *Attorney, Agent, or Firm* — Morgan, Lewis & Bockius LLP

(57) ABSTRACT

The present invention provides a therapeutic agent for progressive disease caused by an increase in Eomes-positive CD4-positive T cells, comprising a compound represented by formula (I) or a salt thereof as an active ingredient. In the formula, $R^1$ is an aldopyranose residue, $R^2$ is a hydrogen atom or a hydroxy group, $R^3$ is $—CH_2—$, $—CH(OH)—CH_2—$, or $—CH{=}CH—$, $R^4$ is a hydrogen atom or $CH_3$, x is 0 to 35, and y and z each are an integer satisfying y+z=0 to 3.

[Chemical Formula 1]

(I)

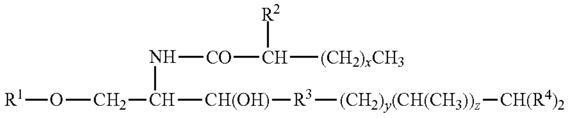

10 Claims, 7 Drawing Sheets

(56) References Cited

OTHER PUBLICATIONS

Comi, "Disease-modifying treatments for progressive multiple sclerosis," Multiple Sclerosis Journal, 19 (11): 1428-1436 (2013).
Miyamoto et al., "A synthetic glycolipid prevents autoimmune encephalomyelitis by inducing TH2 bias of natural killer T cells," Nature, 413: 531-534 (2001).
Araki et al., "Th2 bias of CD4+ Nkt Cells derived from multiple sclerosis in remission," International Immunology, 15 (2): 279-288 (2003).
Raveney et al., "Eomesodermin-expressing T-helper cells are essential for chronic neuroinflammation," Nature Communications, 6: 8437 (2015).
Zhang et al., "Extrapituitary prolactin promotes generation of Eomespositive helper T cells mediating neuroinflammation," PNAS, 116 (42): 21131-21139 (2019).
Doi et al., "Orphan nuclear receptor NR4A2 expressed in T cells from multiple sclerosis mediates production of inflammatory cytokines," PNAS, 105 (24): 8381-8386 (2008).
Takahashi et al., "Natural killer type 2 bias in remission of multiple sclerosis," The Journal of Clinical Investigation, 107 (5): p. R23-p. R29 (2001).
Matsui, "Progress in unravelling the etiology of multiple sclerosis? ," Clinical Neurology, 48 (11): 849-852 (2008) (see English abstract).
Cui et al., "NKT Cells in Neurological Diseases," Frontiers in Cellular Neuroscience, 13: Article 245 (2019).
Van Kaer et al., "Natural killer T cells in multiple sclerosis and its animal model, experimental autoimmune encephalomyelitis," Immunology, 146: 1-10 (2015).
Sekiya et al., "The nuclear orphan receptor Nr4a2 induces Foxp3 and regulates differentiation of CD4 + T cells," Nature Communications, 2: Article 269, 1-12 (2011).
Sakuishi et al., "Role of NK Cells and Invariant NKT Cells in Multiple Sclerosis," Results and Problems in Cell Differentiation, 51: 127-147 (2010).
Okamoto et al., "Current status and issues of 'efficacy and safety of OCH-NCNP1 in patients with relapsing multiple sclerosis',https://doi.org/10.15082/jsnt.37.6_S93", Neurological Therapeutics, Oct. 5, 2020,vol. 37,No. 6, p. S93.
About efficacy and safety of OCH-NCNP1 in patients with relapsing multiple sclerosis,https://www.neurologyjp.org/news/pdf/news_20191213_01_01.pdf, Japanese Society of Neurological Therapeutics website, Dec. 4, 2019.
"Phase II Clinical Trial of OCHNCNP1," https://www.clinicaltrials.gov/ct2/show/NCT04211740, ClinicalTrials.gov, Aug. 4, 2020.
Ifergan et al., "Targeting the GM-CSF receptor for the treatment of CNS autoimmunity", Journal of Autoimmunity, vol. 84, Nov. 2017, pp. 1-25.

* cited by examiner

THERAPEUTIC AGENT FOR PROGRESSIVE DISEASE CAUSED BY INCREASE IN EOMES-POSITIVE CD4-POSITIVE T CELLS

TECHNICAL FIELD

The present invention relates to a therapeutic agent for progressive disease caused by an increase in Eomes-positive CD4-positive T cells.

BACKGROUND ART

In cytotoxic T cells (CTL: CD8-positive T cells) and NK cells, it is known that the Eomes gene expressed on the cell surface controls the production and release of perforin and granzyme B (refer to Non Patent Literature 1). In addition, it has been reported that expression of the Eomes gene in some CD4-positive T cells is associated with anti-tumor immunity or chronic viral diseases (refer to Non Patent Literatures 2 and 3).

In recent years, it has been reported that CD4-positive T cells collected from patients suffering from progressive diseases such as secondary progressive multiple sclerosis show increased levels of Eomes gene and protein expression.

The present inventors found that in NR4A2-deficient mice in which monophasic experimental autoimmune encephalomyelitis (EAE) was induced, EAE pathology accompanied by normally-observed limb paralysis was not observed in the early stages of induction, whereas EAE pathology (hereinafter also referred to as "late EAE pathology") is observed during the late stage of EAE (about 28 days after induction or later), and the late EAE pathology becomes a model for progressive MS pathology (Patent Literature 1). In addition, the present inventors thought that neurodegeneration associated with the late EAE pathology is caused by sustained neuronal cell damage due to the release of granzyme B from T cells following stimulation and found that the late EAE pathology is improved by inhibiting the PAR1 receptor by using a PAR1 receptor antagonist or the like (Patent Literature 2). Furthermore, the present inventors newly found that in the late EAE pathology of NR4A2-deficient mice, stimulation of Th cells with CNS-derived antigen-presenting cells promotes the induction of Eomes molecule expression in those Th cells, and prolactin produced by antigen-presenting cells promotes the induction of Eomes molecule expression, and found that the late EAE pathology is improved by inhibiting prolactin (Patent Literature 3).

CITATION LIST

Patent Literature

Patent Literature 1: WO 2016/002827 A1
Patent Literature 2: WO 2016/114386 A1
Patent Literature 3: WO 2018/101261 A1

Non Patent Literature

Non Patent Literature 1: Science 2003, 302: 1041-1043.
Non Patent Literature 2: Eur. J. Immunol. 2019, 49: 38-41.
Non Patent Literature 3: J Leukoc Biol. 95(5), May 2014: 705-713.
Non Patent Literature 4: Nature Reviews Neurology 2012, 8: 647-656.
Non Patent Literature 5: Nature Reviews Neurology 2013, 9: 496-503.
Non Patent Literature 6: Multiple Sclerosis Journal, 2013, 19: 1428-1436.

SUMMARY OF INVENTION

Technical Problem

An object of the present invention is to provide a therapeutic agent for progressive disease caused by an increase in Eomes-positive CD4-positive T cells.

Solution to Problem

The present inventors have newly found that the expression of Eomes-positive T cells is induced in the late EAE pathology in NR4A2-deficient mice, and that the compound represented by the formula (I) or a salt thereof suppresses the induction of Eomes molecule expression.

The present invention provides the following (1) to (8).

(1) A therapeutic agent for progressive disease caused by an increase in Eomes-positive T cells, comprising a compound represented by formula (I) or a salt thereof as an active ingredient:

[Chemical Formula 1]

(I)

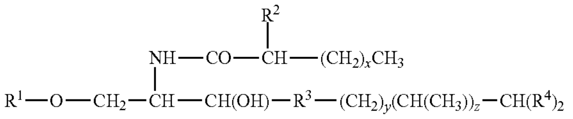

wherein $R^1$ is an aldopyranose residue, $R^2$ is a hydrogen atom or a hydroxy group, $R^3$ is $—CH_2—$, $—CH(OH)—CH_2—$, or $—CH{=}CH—$, $R^4$ is a hydrogen atom or $CH_3$, x is 0 to 35, and y and z each are an integer satisfying y+z=0 to 3.

(2) The therapeutic agent for progressive disease according to (1), wherein $R^1$ is represented by the following formula (II):

[Chemical Formula 2]

(II)

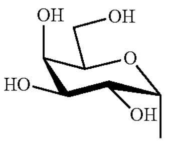

(3) The therapeutic agent for progressive disease according to (1) or (2), wherein $R^2$ and $R^4$ each are a hydrogen atom, x is 11 to 23, and z is 0.

(4) The therapeutic agent for progressive disease according to any one of (1) to (3), wherein the compound represented by the formula (I) or a salt thereof is a compound represented by formula (III) or a salt thereof:

[Chemical Formula 3]

(III)

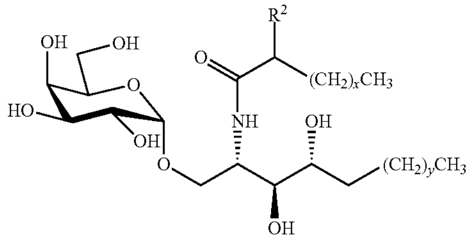

wherein $R^2$ is a hydrogen atom, x is 12 to 23, and y is an integer satisfying 0 to 3.

(5) The therapeutic agent for progressive disease according to any of (1) to (4), wherein the progressive disease is relapsing-remitting multiple sclerosis, progressive relapsing multiple sclerosis, primary progressive multiple sclerosis, or secondary progressive multiple sclerosis.

(6) A method for treating a progressive disease caused by an increase in Eomes-positive CD4-positive T cells, the method comprising administering a composition comprising the compound represented by formula (I) or a salt thereof.

(7) The method for treating a progressive disease according to (5), comprising orally administering a composition containing the compound represented by the formula (I) or a salt thereof.

(8) The method for treating a progressive disease according to (6) or (7), wherein the progressive disease is relapsing-remitting multiple sclerosis, progressive relapsing multiple sclerosis, primary progressive multiple sclerosis, or secondary progressive multiple sclerosis.

Advantageous Effects of Invention

According to the present invention, it is possible to provide a therapeutic agent for progressive disease caused by an increase in Eomes-positive CD4-positive T cells.

BRIEF DESCRIPTION OF DRAWINGS

FIG. 5(*a*) is a diagram in case where 400 μg/kg of OCH is administered, and FIG. 5(*b*) is a diagram in case where 40 μg/kg of OCH is administered.

DESCRIPTION OF EMBODIMENTS

Definition

Figure 1:
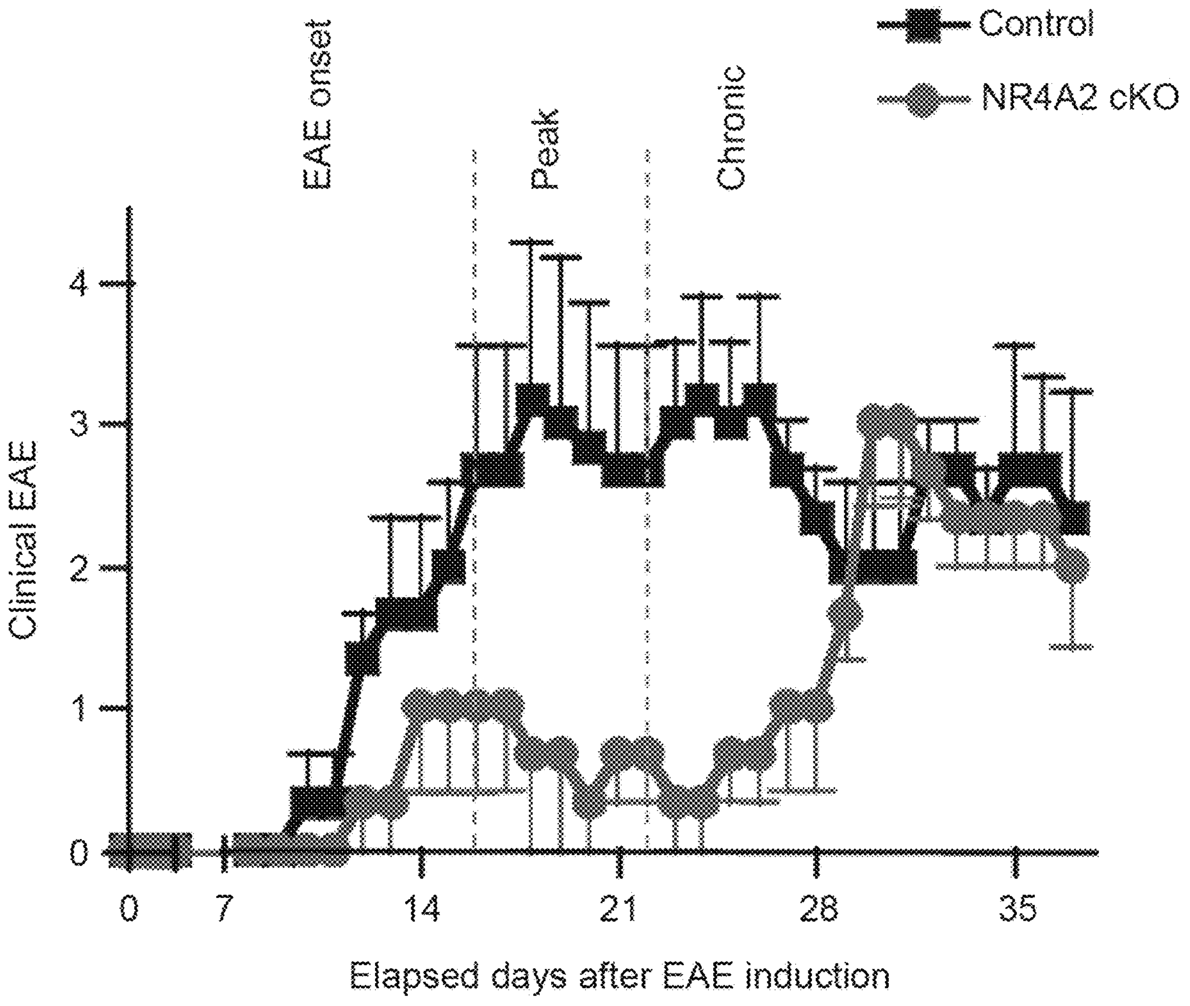
FIG. 1 is a diagram showing the EAE scores of NR4A2-deficient mice and control mice in which EAE was induced by $MOG_{35-55}$ peptide sensitization.

As used herein, the term "progressive disease caused by an increase in Eomes-positive CD4-positive T cells" means a progressive disease caused by an increase in CD4-positive T cells in which the Eomes gene and the protein encoded by the Eomes gene are expressed in the cell. Examples of the progressive disease caused by an increase in Eomes-positive CD4-positive T cells includes progressive multiple sclerosis (for example, primary progressive MS (PP-MS), secondary progressive multiple sclerosis (SP-MS), relapsing-remitting MS), autoimmune optic neuritis, chronic inflammatory demyelinating polyneuropathy (CIDP), and myalgic encephalomyelitis/chronic fatigue syndrome.

Multiple sclerosis (MS) is one of the autoimmune diseases, and is a disease in which multiple inflammations targeting myelin sheaths and nerve axons are induced in the central nervous system, causing nerve conduction disorders due to extensive demyelination. As the pathological condition of multiple sclerosis progresses, severe neurological symptoms such as movement disorder, higher brain dysfunction, ataxic symptoms, sensory disorder, and visual disorder appear. Multiple sclerosis includes relapsing-remitting MS (RR-MS) in which acute exacerbations and remissions are repeated, and progressive MS. As progressive MS, primary progressive MS (PP-MS), secondary progressive MS (SP-MS) in which RR-MS pathology progresses to progressive disease after a period of time, and progressive relapsing MS (PR-MS) that progresses with repeated relapses are known (refer to Non Patent Literatures 4 to 6).

As a disease-modifying drug (DMD) for RR-MS, type 1 interferons, anti-inflammatory agents, immunosuppressive agents, and the like are known. As the therapeutic agent for progressive MS, anti-CD20 antibodies are currently known, and as the therapeutic agents for RR-MS and SP-MS, S1P receptor modulators are known, but there are still many unclear points about the detailed pathology and mechanism of progressive MS.

[NR4A2 Gene]

The NR4A2 gene, also called Nurr1 gene, NOT gene, or RNR1 gene, is one of orphan nuclear receptors. Expression of the NR4A2 gene was reported first in the central nervous system, and is particularly expressed in the ventral midbrain, brainstem, and spinal cord. In addition, NR4A2 is induced to be expressed in response to prostaglandins, growth factors, inflammatory cytokines, and T-cell receptor cross-linking, and directly binds to DNA in a ligand-dependent or ligand-independent manner to control transcription. The NCBI Reference Sequence accession number for the transcript of the human NR4A2 gene is NM_006186.3.

The present inventors investigated changes in the expression level of each gene in T cells collected from multiple sclerosis patients or healthy adults, and found that the expression of the NR4A2 gene is significantly increased in T cells collected from multiple sclerosis patients. The present inventors also found that the expression of NR4A2 gene induces production of interleukin 17 and is important for the function of Th17 cells involved in the pathology of various autoimmune diseases such as multiple sclerosis (Raveney et al., PLoS One, 8(2), 2013: e56595). Furthermore, the present inventors found that mice lacking the NR4A2 gene specifically for CD4-positive T cells, that is, NR4A2 conditional knockout mice (NR4A2 cKO mice), were used to induce experimental autoimmune encephalomyelitis (EAE), and unlike normal EAE models, clinical scores do not increase around 14 days after EAE induction, and clinical scores increase 28 days after induction (refer to Patent Literatures 1 and 2). Thus, the experimental autoimmune encephalomyelitis (EAE) model using NR4A2 cKO mice can be used as a Th17 cell-independent pathologic model of progressive immune demyelinating disease, particularly an animal model that shows the late stage (progressive stage) pathology of progressive MS.

Herein, conditional knockout (cKO) means deletion of target genes in specific tissues and specific cells of non-human animals, unlike deletion of all desired genes. Examples thereof include mice specifically deficient in the NR4A2 gene in $CD4^+$ T cells.

NR4A2 cKO mice can be established, for example, by Cre-loxP site-specific recombination techniques. Specifically, NR4A2 cKO mice can be produced by crossbreeding mice introduced with two loxP genes so as to sandwich the NR4A2 gene, which is the target gene to be deleted, and mice into which a cre gene has been introduced downstream of the promoter region of the target cell so that the Cre enzyme is expressed in the cell where the target gene is to be deleted. A tissue or cell deficient in the target gene can be selected by those skilled in the art according to the purpose. For example, if the target cells are $CD4^+$ T cells, it is possible to produce mice deficient in the NR4A2 gene only in $CD4^+$ T cells.

Recent studies have revealed that Th17 cells (particularly NR4A2-positive Th17 cells) are involved in early EAE pathology, but in late EAE pathology, IL-17 production levels were insufficient to cause EAE pathology. Furthermore, investigation of CNS-infiltrating $CD4^+$ T cells revealed that Eomes gene expression was significantly enhanced around 28 days after EAE induction. $Eomes^+$ $CD4^+$ T cells did not express IL-17, suggesting a subset different from Th17 cells. In addition, intravenous administration of Eomes-specific siRNA to EAE-induced NR4A2 cKO mice significantly improved late EAE pathology, and NR4A2/Eomes-deficient mice did not develop late EAE pathology, assuming that improvement of the late EAE pathology is associated with suppression of Eomes gene expression.

[Eomes Gene]

The Eomes gene, also called Eomesodermin or Tbr2, is a member of the T-box transcription factor family and is a protein involved in the development and differentiation of vertebrates. The Eomes gene is known to be expressed in $CD8^+$ T cells (cytotoxic T cells, CTL) and NK cells. It is also known to directly induce perforin and granzyme B expression. The NCBI Reference Sequence accession numbers for transcripts of the human Eomes gene are NM_001278182.1 (variant 1), NM_005442.3 (variant 2), and NM_001278183.1 (variant 3).

[Therapeutic Agent for Progressive Immune Demyelinating Disease]

The first embodiment of the present invention is a therapeutic agent for progressive disease caused by an increase in Eomes-positive T cells, therapeutic agent comprising the compound represented by the formula (I) or a salt thereof as an active ingredient.

The compound represented by the formula (I) is a kind of α-galactosylceramide. The compound represented by the formula (I) includes all stereoisomers (for example, enantiomers, diastereomers) derived from quaternary carbon atoms. The compound represented by the formula (I) may be a mixture thereof (for example, racemate).

[Chemical Formula 4]

(I)

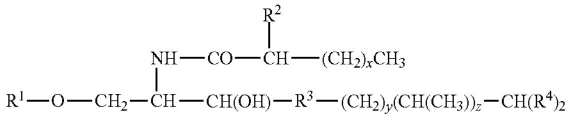

In the formula (I), $R^1$ is an aldopyranose residue. Examples of the aldopyranose residue include α-D-glucosyl, α-D-galactosyl, α-D-mannosyl, β-D-glucosyl, β-D-galactosyl, β-D-mannosyl, 2-deoxy-2-amino-α-D-galactosyl, 2-deoxy-2-amino-β-D-galactosyl, 2-deoxy-2-acetylamino-α-D-galactosyl, 2-deoxy-2-acetylamino-β-D-galactosyl, β-D-allopyranosyl, β-D-altropyranosyl, and β-D-idosyl. The aldopyranose group represented by $R^1$ is preferably α-form, more preferably α-D-galactopyranosyl represented by following formula (II).

[Chemical Formula 5]

(II)

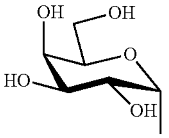

In the formula (I), $R^2$ is a hydrogen atom (—H) or a hydroxy group (—OH), and is preferably a hydrogen atom is preferable.

In the formula (I), $R^3$ is $—CH_2—$, $—CH(OH)—CH_2—$, or —CH═CH—, preferably $—CH_2—$ or $—CH(OH)—CH_2—$, and more preferably $—CH(OH)—CH_2—$.

In the formula (I), $R^4$ is a hydrogen atom (—H) or $CH_3$, and is preferably a hydrogen atom.

In the formula (I), x is an integer of 0 to 35, preferably an integer of 0 to 26, more preferably an integer of 11 to 26, further preferably an integer of 11 to 23, and particularly preferably an integer of 18 to 23.

In the formula (I), y and z are integers satisfying y+z=0 to 3. Preferably, z is 0 and y is 0 to 3. More preferably, z is 0 and y is 1 to 3. Note that $—(CH_2)_y(CH(CH_3))_z—$ does not mean that the order of $(CH_2)$ and $(CH(CH_3))$ follows the described order, but simply shows the quantitative relationship between $(CH_2)$ and $(CH(CH_3))$. For example, if y=2 and z=1, it means that there are two $(CH_2)$ and one (CH(CH 3)) in $—(CH_2)_y(CH(CH_3))_z—$, and the arrangement of two $(CH_2)$ and one $(CH(CH_3))$ does not matter. Specifically, any of $—CH(CH_3)CH_2CH_2—$, $—CH_2CH(CH_3)CH_2—$, or $—CH_2CH_2CH(CH_3)—$ may be possible.

The compound represented by the formula (I) or a salt thereof is preferably a compound represented by the formula (III) or a salt thereof:

[Chemical Formula 6]

(III)

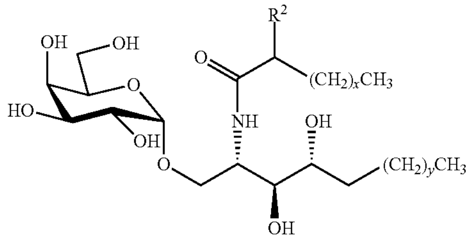

wherein $R^2$ is a hydrogen atom or a hydroxy group, and is preferably a hydrogen atom. x is 12 to 23, preferably 15 to 23, and more preferably 18 to 23. y is 1, 2, or 3, preferably 2 or 3.

Specific examples of the compound represented by formula (I) include the compounds described in (1) to (48) below. Compounds (3) to (9), (15) to (21), (27) to (33), and (39) to (45) are more preferable as active ingredients according to the present embodiment.

(1) (2S,3S,4R)-1-O-(α-D-galactosyl)-2-(N-triacontanoylamino)-1,3,4-heptanetriol,
(2) (2S,3S,4R)-1-O-(α-D-galactosyl)-2-(N-nonacosanoylamino)-1,3,4-heptanetriol,
(3) (2S,3S,4R)-1-O-(α-D-galactosyl)-2-(N-octacosanoylamino)-1,3,4-heptanetriol,
(4) (2S,3S,4R)-1-O-(α-D-galactosyl)-2-(N-heptacosanoylamino)-1,3,4-heptanetriol,
(5) (2S,3S,4R)-1-O-(α-D-galactosyl)-2-(N-hexacosanoylamino)-1,3,4-heptanetriol,
(6) (2S,3S,4R)-1-O-(α-D-galactosyl)-2-(N-pentacosanoylamino)-1,3,4-heptanetriol,
(7) (2S,3S,4R)-1-O-(α-D-galactosyl)-2-(N-tetracosanoylamino)-1,3,4-heptanetriol,
(8) (2S,3S,4R)-1-O-(α-D-galactosyl)-2-(N-tricosanoylamino)-1,3,4-heptanetriol,
(9) (2S,3S,4R)-1-O-(α-D-galactosyl)-2-(N-docosacosanoylamino)-1,3,4-heptanetriol,
(10) (2S,3S,4R)-1-O-(α-D-galactosyl)-2-(N-heneicosanoylamino)-1,3,4-heptanetriol,
(11) (2S,3S,4R)-1-O-(α-D-galactosyl)-2-(N-eicosanoylamino)-1,3,4-heptanetriol,
(12) (2S,3S,4R)-1-O-(α-D-galactosyl)-2-(N-nonadecanoylamino)-1,3,4-heptanetriol,
(13) (2S,3S,4R)-1-O-(α-D-galactosyl)-2-(N-triacontanoylamino)-1,3,4-octanetriol,
(14) (2S,3S,4R)-1-O-(α-D-galactosyl)-2-(N-nonacosanoylamino)-1,3,4-octanetriol,
(15) (2S,3S,4R)-1-O-(α-D-galactosyl)-2-(N-octacosanoylamino)-1,3,4-octanetriol,
(16) (2S,3S,4R)-1-O-(α-D-galactosyl)-2-(N-heptacosanoylamino)-1,3,4-octanetriol,
(17) (2S,3S,4R)-1-O-(α-D-galactosyl)-2-(N-hexacosanoylamino)-1,3,4-octanetriol,
(18) (2S,3S,4R)-1-O-(α-D-galactosyl)-2-(N-pentacosanoylamino)-1,3,4-octanetriol,
(19) (2S,3S,4R)-1-O-(α-D-galactosyl)-2-(N-tetracosanoylamino)-1,3,4-octanetriol,
(20) (2S,3S,4R)-1-O-(α-D-galactosyl)-2-(N-tricosanoylamino)-1,3,4-octanetriol,
(21) (2S,3S,4R)-1-O-(α-D-galactosyl)-2-(N-docosacosanoylamino)-1,3,4-octanetriol,
(22) (2S,3S,4R)-1-O-(α-D-galactosyl)-2-(N-heneicosanoylamino)-1,3,4-octanetriol,
(23) (2S,3S,4R)-1-O-(α-D-galactosyl)-2-(N-eicosanoylamino)-1,3,4-octanetriol,
(24) (2S,3S,4R)-1-O-(α-D-galactosyl)-2-(N-nonadecanoylamino)-1,3,4-octanetriol,
(25) (2S,3S,4R)-1-O-(α-D-galactosyl)-2-(N-triacontanoylamino)-1,3,4-nonanetriol,
(26) (2S,3S,4R)-1-O-(α-D-galactosyl)-2-(N-nonacosanoylamino)-1,3,4-nonanetriol,
(27) (2S,3S,4R)-1-O-(α-D-galactosyl)-2-(N-octacosanoylamino)-1,3,4-nonanetriol,
(28) (2S,3S,4R)-1-O-(α-D-galactosyl)-2-(N-heptacosanoylamino)-1,3,4-nonanetriol,
(29) (2S,3S,4R)-1-O-(α-D-galactosyl)-2-(N-hexacosanoylamino)-1,3,4-nonanetriol,
(30) (2S,3S,4R)-1-O-(α-D-galactosyl)-2-(N-pentacosanoylamino)-1,3,4-nonanetriol,
(31) (2S,3S,4R)-1-O-(α-D-galactosyl)-2-(N-tetracosanoylamino)-1,3,4-nonanetriol,
(32) (2S,3S,4R)-1-O-(α-D-galactosyl)-2-(N-tricosanoylamino)-1,3,4-nonanetriol,
(33) (2S,3S,4R)-1-O-(α-D-galactosyl)-2-(N-docosacosanoylamino)-1,3,4-nonanetriol,
(34) (2S,3S,4R)-1-O-(α-D-galactosyl)-2-(N-heneicosanoylamino)-1,3,4-nonanetriol,
(35) (2S,3S,4R)-1-O-(α-D-galactosyl)-2-(N-eicosanoylamino)-1,3,4-nonanetriol,
(36) (2S,3S,4R)-1-O-(α-D-galactosyl)-2-(N-nonadecanoylamino)-1,3,4-nonanetriol,

(37)
(2S,3S,4R)-1-O-(α-D-galactosyl)-2-(N-triacontanoylamino)-1,3,4-hexanetriol,
(38)
(2S,3S,4R)-1-O-(α-D-galactosyl)-2-(N-nonacosanoylamino)-1,3,4-hexanetriol,
(39)
(2S,3S,4R)-1-O-(α-D-galactosyl)-2-(N-octacosanoylamino)-1,3,4-hexanetriol,
(40)
(2S,3S,4R)-1-O-(α-D-galactosyl)-2-(N-heptacosanoylamino)-1,3,4-hexanetriol,
(41)
(2S,3S,4R)-1-O-(α-D-galactosyl)-2-(N-hexacosanoylamino)-1,3,4-hexanetriol,
(42)
(2S,3S,4R)-1-O-(α-D-galactosyl)-2-(N-pentacosanoylamino)-1,3,4-hexanetriol,
(43)
(2S,3S,4R)-1-O-(α-D-galactosyl)-2-(N-tetracosanoylamino)-1,3,4-hexanetriol,
(44)
(2S,3S,4R)-1-O-(α-D-galactosyl)-2-(N-tricosanoylamino)-1,3,4-hexanetriol,
(45)
(2S,3S,4R)-1-O-(α-D-galactosyl)-2-(N-docosacosanoylamino)-1,3,4-hexanetriol,
(46)
(2 S,3 S,4R)-1-O-D-galactosyl)-2-(N-heneicosanoylamino)-1,3,4-hexanetriol,
(47)
(2 S,3 S,4R)-1-O-D-galactosyl)-2-(N-eicosanoylamino)-1,3,4-hexanetriol, and
(48)
(2 S,3 S,4R)-1-O-D-galactosyl)-2-(N-nonadecanoylamino)-1,3,4-hexanetriol.

"A salt of the compound represented by the formula (I)" means a salt prepared by mixing the compound represented by the formula (I) with a base or an acid to form a salt between a specific substituent in the chemical structure represented by the formula (I) and a base or acid. The above salt can be classified into a basic addition salt and an acid addition salt depending on the base or acid used. The base or acid is preferably a pharmaceutically acceptable base or acid. That is, the salt of the compound represented by the formula (I) is preferably a pharmaceutically acceptable salt of the compound represented by the formula (I).

Examples of the basic addition salt include: an alkali metal salt such as a sodium salt or potassium salt; an alkaline earth metal salt such as a calcium salt or magnesium salt; an aliphatic amine salt such as a trimethylamine salt, a triethylamine salt, a dicyclohexylamine salt, an ethanolamine salt, a diethanolamine salt, a triethanolamine salt, or a procaine salt; an aralkylamine salt such as N,N-dibenzylethylenediamine; a heterocyclic aromatic amine salt such as a pyridine salt, a picoline salt, a quinoline salt, or an isoquinoline salt; a basic amino acid salt such as an arginine salt or a lysine salt; an ammonium salt; or a quaternary ammonium salt such as a tetramethylammonium salt, a tetraethylammonium salt, a benzyltrimethylammonium salt, a benzyltriethylammonium salt, a benzyltributylammonium salt, a methyltrioctylammonium salt, or a tetrabutylammonium salt.

Examples of the acid addition salt include: an inorganic acid salt such as a hydrochloride, a sulfate, a nitrate, a phosphate, a carbonate, a bicarbonate, or a perchlorate; an organic acid salt such as an acetate, a propionate, a lactate, a maleate, a fumarate, a tartrate, a malate, a citrate, or an ascorbate; a sulfonate such as a methanesulfonate, an isethionate, a benzenesulfonate, or a p-toluenesulfonate; or an acidic amino acid such as an aspartate and a glutamate.

In the present description, the compound represented by the formula (I) itself does not exert a pharmacological action, but may be a compound that changes the chemical structure thereof by an enzyme or the like after being administered in vivo, and that can provide a desired pharmacological activity. That is, the compound represented by the formula (I) may also include a prodrug form.

The therapeutic agent for progressive disease according to the present embodiment can be composed only of the compound represented by the formula (I) or a salt thereof as an active ingredient, but may comprise, other than the above compound, a pharmaceutically acceptable carrier and/or solvent.

The "pharmaceutically acceptable carrier" refers to the substance, the use of which is acceptable in the field of pharmaceutical technology because of having no or very small adverse effects such as adverse reactions on animals including humans. For example, it refers to a nontoxic excipient, a binder, a disintegrant, a filler, an emulsifier, and a flow control additive, or the like that may be usually used in the field of pharmaceutical technology.

Examples of the excipient include a sugar (for example, but not limited to, glucose, sucrose, lactose, raffinose, mannitol, sorbitol, inositol, dextrin, maltodextrin, starch, and cellulose); a metal salt (for example, sodium chloride, sodium phosphate, calcium phosphate, calcium sulfate, magnesium sulfate, and calcium carbonate); citric acid; tartaric acid; glycine; low-, middle-, or high-molecular weight polyethylene glycol (PEG); pluronic; kaolin; silicic acid; or combinations thereof.

Examples of the binder include starch glues, syrup, glucose solution, gelatin, tragacanth, methylcellulose, hydroxypropyl methylcellulose, sodium carboxymethylcellulose, shellac, and/or polyvinylpyrrolidone.

Examples of the disintegrant include starch, lactose, carboxymethyl starch, cross-linked polyvinylpyrrolidone, agar, laminaran powder, sodium bicarbonate, calcium carbonate, alginic acid or sodium alginate, polyoxyethylene sorbitan fatty acid ester, sodium lauryl sulfate, monoglyceride stearate, or a salt thereof.

Examples of the filler include the sugar described above and/or calcium phosphate (for example, tricalcium phosphate or calcium hydrogen phosphate).

Examples of the emulsifier include sorbitan fatty acid ester, glycerin fatty acid ester, sucrose fatty acid ester, and propylene glycol fatty acid ester.

Examples of the flow control additive and the lubricant include silicate, talc, stearate, or polyethylene glycol.

In addition to the above, the pharmaceutically acceptable carrier can also optionally include a tonicity agent, a lubricant, a corrigent, a solubilizer, a suspending agent, a diluent, a surfactant, a stabilizer, an absorption promoter (for example, a quaternary ammonium salt and sodium lauryl sulfate), an expander, a pH adjuster, a humectant (for example, glycerin and starch), an adsorbent (for example, starch, lactose, kaolin, bentonite, and colloidal silicic acid), a disintegration inhibitor (for example, saccharose, stearin, cocoa butter, and hydrogenated oil), a coating agent, a coloring agent, a preservative, an antioxidant, a fragrance, a flavor, a sweetener, a buffer, a soothing agent, and the like.

The "pharmaceutically acceptable solvent" refers to the solvent, the use of which is acceptable in the field of pharmaceutical technology because of having no or very small adverse effects such as adverse reactions on animals including humans. For example, the above solvent is a nontoxic solvent that can be commonly used in the field of pharmaceutical technology, and examples thereof include water, ethanol, propylene glycol, ethoxylated isostearyl alcohol, polyoxylated isostearyl alcohol, and polyoxyethylene sorbitan fatty acid esters. These are preferably adjusted to be isotonic to blood.

The above carrier and solvent are mainly used for facilitating the formulation and administration, and maintaining the dosage forms and pharmaceutical effects, and can be used appropriately as necessary.

[Method for Producing Compound Represented by Formula (I)]

The compound represented by the formula (I) can be produced by various methods known in the art, for example, the method described in Japanese Patent No. 4064346 or Japanese Patent No. 4742220.

[Method for Producing Therapeutic Agent for Progressive Disease Caused by Increase in Eomes-Positive CD4-Positive T Cells]

As for the therapeutic agent for progressive disease according to the present embodiment, a preparation for improving or treating a progressive disease caused by an increase in Eomes-positive CD4-positive T cells by utilizing a compound represented by the formula (I) or a salt thereof, and using a method known in the art. For example, the method described in Remington's Pharmaceutical Sciences (Merck Publishing Co., Easton, Pa.) may be used for the formulation.

The dosage form of the therapeutic agent for progressive disease caused by an increase in Eomes-positive CD4-positive T cells is appropriately selected according to the administration method and/or the prescription condition. The administration method can be broadly divided into oral administration and parenteral administration.

Examples of the dosage form suitable for oral administration include a tablet, a pill, a granule, a powder, a capsule, a drop, a sublingual agent, a lozenge, and a liquid.

The tablet can optionally be a coated tablet known in the art, such as a sugar-coated tablet, a gelatin-coated tablet, an enteric coated tablet, a film-coated tablet, and a bilayer tablet or multilayer tablet. For example, the capsule may be prepared by mixing a pulverized active ingredient with an excipient such as lactose, starch or a derivative thereof, or a cellulose derivative, and packing the mixture into a gelatin capsule. In addition, the tablet may be prepared by adding a binder such as sodium carboxymethylcellulose, alginic acid or gum arabic and water, in addition to the above excipient, kneading the resultant, optionally making a granule, then further adding a lubricant such as talc or stearic acid, and using a usual compression tableting machine. In the case of oral administration, the shape and size of each dosage form described above can both fall within the range known in the art and are not particularly limited.

Examples of the dosage form suitable for a parenteral preparation include a solution (including a suspension), an emulsion (a cream), a gel, an ointment (including a paste), a plaster, a powder, and a suppository. These can be prepared as a dosage form suitable for the administration method thereof, such as systemic administration, local administration, or transrectal administration. Examples of the dosage form suitable for systemic administration include a solution as an injection. In the case of injection, an injection preparation are prepared by dissolving the active ingredient together with a solubilizing agent in sterilized distilled water or sterilized physiological saline, and filling the resultant into an ampule. They may optionally contain a stabilizer and a buffering substance. Examples of the dosage form suitable for local administration can include a solution as an eye drop or a nasal drop, an emulsion, a powder as a nasal drop, a paste, a gel, an ointment, and a plaster. Examples of the dosage form suitable for transrectal administration can include a suppository.

It is preferable that an effective amount of the active ingredient should be contained in the therapeutic agent for progressive disease of one dosage unit. As used herein, the term "effective amount" refers to an amount necessary for the active ingredient to exert the function thereof, that is, an amount necessary for the compound represented by the formula (I) or a salt thereof to suppress the growth of Eomes-positive CD4-positive T cells or reduce the intracellular Eomes expression level of T cells, and an amount that imparts few or no adverse reactions to the subject that receives administration. This effective amount may vary depending on various conditions such as subject information, dosage form, and route of administration. The "subject information" refers to the degree of progression or severity of disease, general health conditions, age, body weight, sex, diet, drug sensitivity, presence or absence of a concurrent drug, resistance to treatment, and the like. As a specific example of the effective amount of the therapeutic agent for progressive disease according to the present embodiment, in the case of administering orally the therapeutic agent for progressive disease according to the present embodiment to a human adult man (body weight: 60 kg), one dosage unit can contain 0.01% by weight to 100% by weight, preferably 0.1% by weight to 100% by weight of the active ingredient. In addition, in the case of administering the therapeutic agent for progressive disease according to the present embodiment through an injection solution one dosage unit of the injection solution can contain 0.01% (w/v) to 20% (w/v), preferably 0.1% (w/v) to 10% (w/v) of the active ingredient. In the case of the dosage form such as a tablet, a pill, or a capsule, the effective amount of Eomes-positive CD4-positive T cells permits divided administration that is adjusted depending on the number of dosage forms, and thus it is not necessary to contain an effective amount in one tablet.

The second embodiment of the present invention is a method for treating a progressive disease caused by an increase in Eomes-positive CD4-positive T cells, the method comprising administering a composition comprising the compound represented by the formula (I) or a salt thereof.

In the present embodiment, the definitions of "compound represented by the formula (I) or a salt thereof" and "progressive disease caused by an increase in Eomes-positive CD4-positive T cells" can be referred to the definitions described in the first embodiment. A composition comprising the compound represented by the formula (I) or a salt thereof may be a therapeutic agent for progressive diseases shown in the first embodiment.

[Administration Method]

An organism that receives a composition comprising a compound represented by the formula (I) or a salt thereof (for example, a therapeutic agent for progressive disease shown in the first embodiment) is a vertebrate, preferably a mammal, more preferably a human.

Particular modes of administration include oral administration or parenteral administration, as described above. The parenteral administration is further divided into systemic administration and local administration (for example, subcutaneous administration, percutaneous administration, transmucosal administration, or transrectal administration).

The administration method can be appropriately selected according to the onset site or the degree of progression of the disease, etc., and may be either systemic administration or local administration. Preferred is low invasive oral administration. In addition, in the case of rapidly spreading the active ingredient via the circulatory system such as the blood flow, systemic administration mediated by injection into a blood vessel is suitable. If the target disease is local, the local administration for direct administration to the onset site and its neighborhood by local injection can also be adopted. The injection site of the pharmaceutical composition by injection is not particularly limited. Examples thereof include a site within the circulatory system such as a site within the blood vessel or a site within the ventricle and a site within an organ or tissue such as intrahepatic site, intramuscular site, intraarticular site, intramedullary site, intraspinal site, percutaneous site, subcutaneous site, intradermal site, intraperitoneal site, intranasal site, intraintestinal site, and sublingual site.

The term "therapeutic agent" means an agent that refers to both therapeutic treatment and prophylactic or preventative measures, and this purpose means treating, preventing, or slowing (mitigating) undesirable physiological changes or disorders such as the development, spread, or progression of progressive disease.

EXAMPLES

The present invention will be described more specifically based on examples. However, the present invention is not limited to the following examples.

1. EAE Analysis of NR4A2 cKO Mice (1) Animals

All mice used were 6 to 8 weeks old and housed under specific pathogen-free conditions. NR4A2$^{fl/fl}$ mice were established by using a targeting vector flanking the NR4A2 gene with loxp sequences. That is, the NR4A2 transgene flanked by loxp sequences was introduced into C57BL/6 embryonic stem cells by microinjection. The established lines were crossed with C57BL/6 FLPe mice (Riken BioResource Center), and the strains from which the neomycin cassette was removed were crossed to produce homozygous NR4A2$^{fl/fl}$ C57BL/6 mice. The resulting mice were mated with C57BL/6 CD4-Cre mice (Taconic Biosciences, Inc.) to establish CD4-specific NR4A2 cKO C57BL/6 mice (C57BL/6 Cre-CD4/NR4A2$^{fl/fl}$ mice). In addition, the resulting mice were mated (backcrossed) with SJL/J mice (female, Charles River Japan, Inc.) for 10 generations to establish NR4A2$^{fl/fl}$ SJL mice and CD4-specific NR4A2 cKO SJL mice (SJL/J Cre-CD4/NR4A2$^{fl/fl}$ mice).

Eomes$^{fl/fl}$ mice purchased from The Jackson Laboratory were mated with C57BL/6 CD4-Cre mice to obtain Cre-CD4 Eomes$^{fl/fl}$ C57BL/6 mice. Furthermore, Eomes$^{fl/fl}$ mice were mated with Cre-CD4/NR4A2$^{fl/fl}$ C57BL/6 mice to obtain Cre-CD4/NR4A2$^{fl/fl}$ Eomes$^{fl/fl}$ C57BL/6 mice.

(2) EAE Induction (Monophasic EAE)

A peptide of 100 μg corresponding to $MOG_{35-55}$ residues (synthesized at Toray Research Center, Tokyo, Japan; hereinafter also referred to as "MOG peptide") and 1 mg of killed Mycobacterium tuberculosis H37Ra (Difco Laboratories, Kansas, USA) were emulsified with complete Freund's adjuvant, respectively, then were mixed in the same amount, and the mixture was emulsified by using a homogenizer to prepare an MOG emulsion. The obtained MOG emulsion was subcutaneously injected into the dorsum of CD4-specific NR4A2 cKO C57BL/6 mice (Cre-CD4/NR4A2$^{fl/fl}$ C57BL/6 mice, NR4A2 cKO) and the dorsum of NR4A2$^{fl/fl}$ C57BL/6 mice as controls (Control) at one or two sites to confer immunization. In addition, on 0th day and 2nd day after immunization, mice were intraperitoneally injected with 200 ng of pertussis toxin (List Biological Laboratories, USA) in 200 μL of PBS solution per mouse. After injection, mice were evaluated daily for EAE pathology according to the EAE evaluation criteria given below.

<EAE Evaluation Criteria>

0: No clinical signs
1: Partial paralysis of tail
2: Flaccid tail
3: Partial paralysis of hindlimbs
4: Paralysis of all hindlimbs
5: Paralysis of hindlimbs and forelimbs The results are shown in FIG. 1. As shown in FIG. 1, in NR4A2-deficient mice (NR4A2 cKO), the EAE pathology observed in control mice (Control) was improved during the EAE onset, peak, and chronic phases (approximately 9 to 28 days after EAE induction). Meanwhile, in NR4A2-deficient mice, a new pathology (late EAE pathology) appeared 28 days after EAE induction. In the following experiments, 4 to 9 mice were used per group and bars in FIGS. 1 to 7 indicate standard error (SEM).

2. Compound Represented by Formula (I)

In examples, (2S,3S,4R)-1-O-(α-D-galactosyl)-2-(N-tetracosanoylamino)-1,3,4-nonanetriol as the compound represented by the formula (I) (hereinafter also referred to as "OCH") was used. OCH is represented by the following formula.

[Chemical Formula 7]

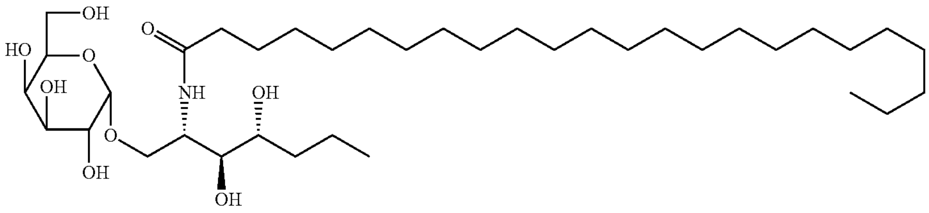

3. Effect of OCH Administration on EAE Pathology (1) Effect of OCH Administration NR4A2-deficient mice to which EAE was induced in the same manner as in 1. (2) described above received OCH or PBS (phosphate buffered saline) at a dose of 400 μg/kg immediately after induction (0th day), and 7 days, 14 days, 21 days, and 28 days after induction, and the mice were evaluated daily for EAE pathology according to the EAE evaluation criteria described above. For comparison, OCH or PBS (phosphate buffered saline) was also administered to monophasic EAE-induced B6 mice, and mice were evaluated daily for EAE pathology. OCH was administered orally as a suspension of PBS, and PBS was also administered orally.

Figure 2:
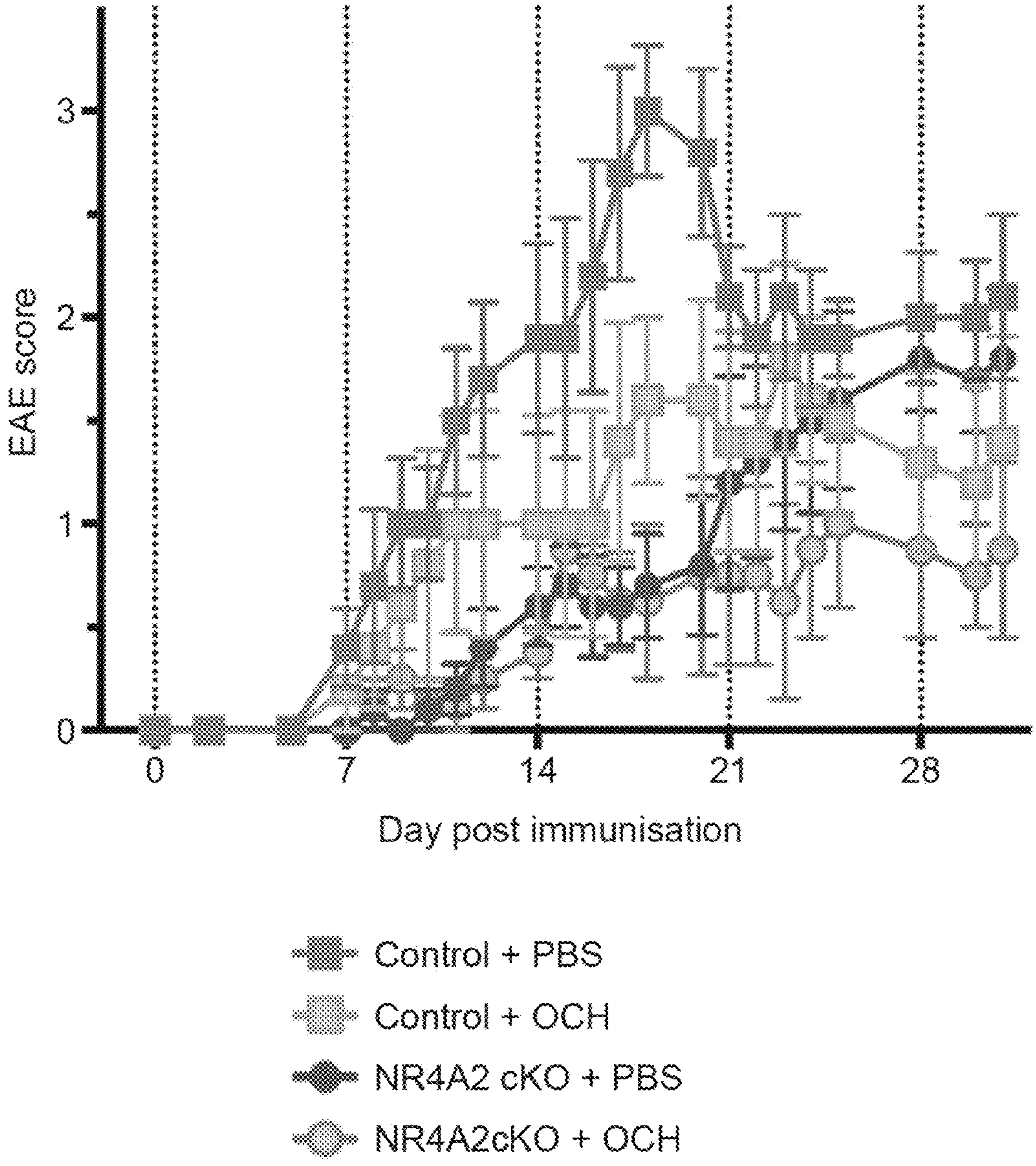
FIG. 2 is a diagram showing the EAE scores of NR4A2-deficient mice and B6 mice in which EAE was induced by $MOG_{35-55}$ peptide sensitization.

The results are shown in FIG. 2. In each model mouse, when the PBS-administered group and the OCH-administered group were compared, administration of OCH improved both early and late EAE pathologies.

(2) Effect of OCH Administration

NR4A2-deficient mice to which monophasic EAE was induced in the same manner as in 1. (2) described above received OCH or PBS (phosphate buffered saline) at a dose of 400 μg/kg 5 days, 10 days, 15 days, 20 days, 25 days, and 30 days after induction, and the mice were evaluated daily for EAE pathology according to the EAE evaluation criteria described above. For comparison, OCH or PBS (phosphate buffered saline) was also administered to monophasic EAE-induced B6 mice, and mice were evaluated daily for EAE pathology. OCH was administered orally as a suspension of PBS, and PBS was also administered orally.

Figure 3:
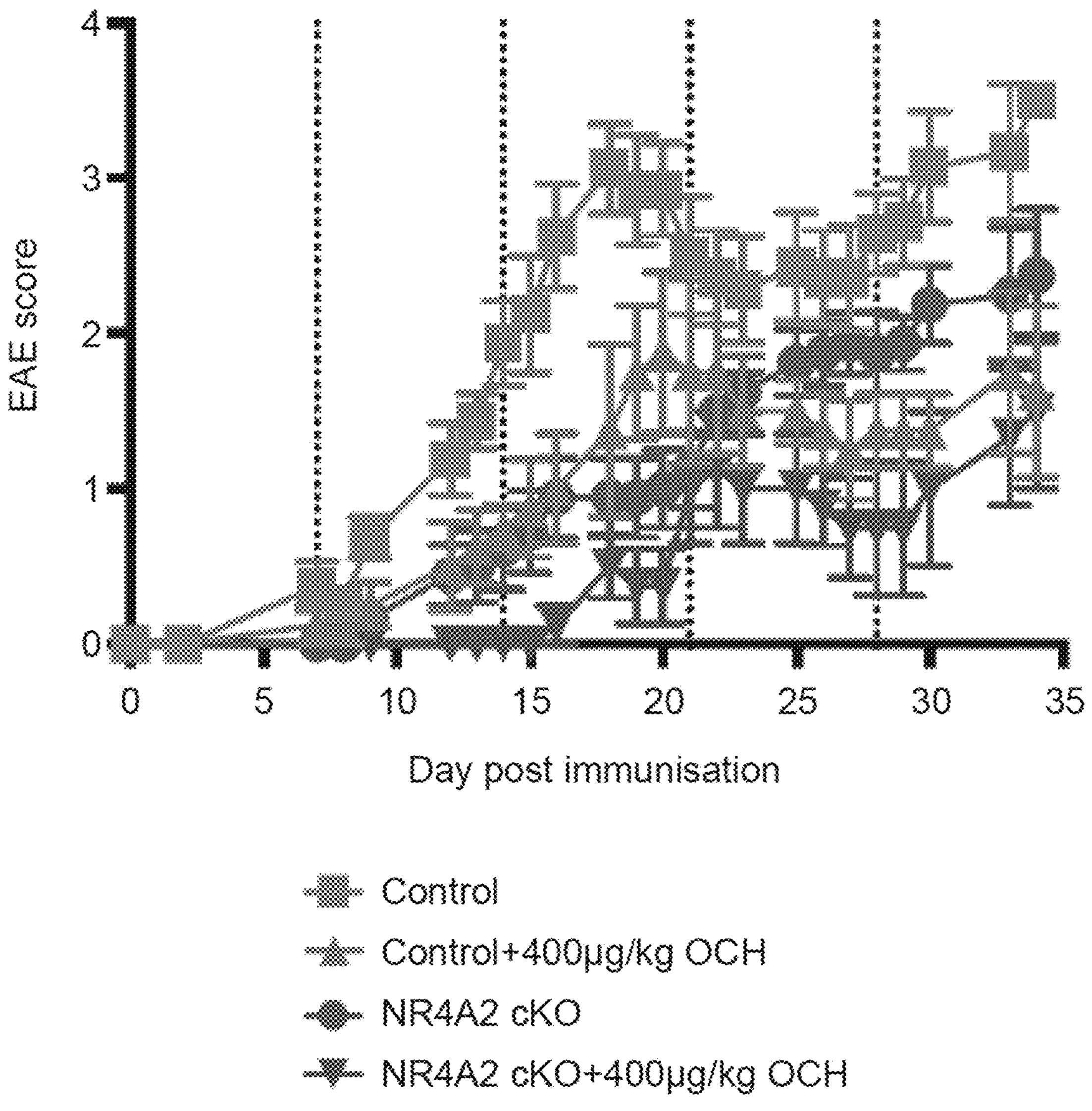
FIG. 3 is a diagram showing the EAE scores of NR4A2-deficient mice and B6 mice in which EAE was induced by $MOG_{35-55}$ peptide sensitization.

The results are shown in FIG. 3. In each model mouse, when the PBS-administered group and the OCH-administered group were compared, administration of OCH improved both early and late EAE pathologies.

(3) Effect of OCH Administration on B6 Mice

B6 mice to which monophasic EAE was induced in the same manner as in 1. (2) described above received OCH at a low dose (40 μg/kg) or a high dose (400 μg/kg) 5 days, 10 days, 15 days, 20 days, 25 days, and 30 days after induction, and the mice were evaluated daily for EAE pathology according to the EAE evaluation criteria described above. For comparison, monophasic EAE-induced B6 mice (without administration) were evaluated daily for EAE pathology. OCH was administered orally as a suspension of PBS, and PBS was also administered orally.

Figure 4:
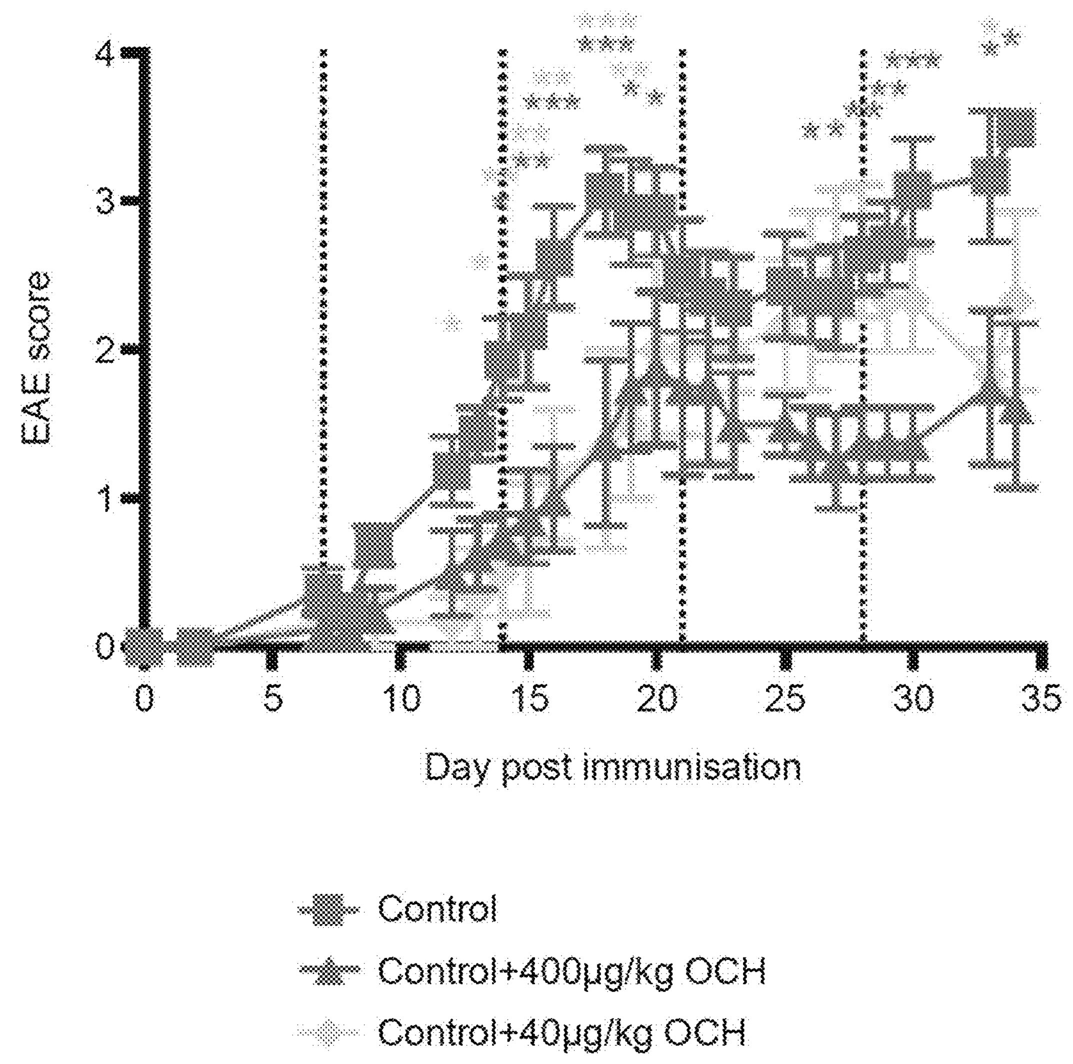
FIG. 4 is a diagram showing the EAE scores of B6 mice in which EAE was induced by $MOG_{35-55}$ peptide sensitization.

The results are shown in FIG. 4. In the B6 mouse EAE model, early EAE pathology was improved in all administration groups, and late EAE pathology was also improved in the high-dose administration group.

(4) Effect of OCH Administration on NR4A2-Deficient Mice

NR4A2-deficient mice to which monophasic EAE was induced in the same manner as in 1. (2) described above received OCH at a dose of 40 μg/kg or 400 μg/kg 5 days, 10 days, 15 days, 20 days, 25 days, and 30 days after induction, and the mice were evaluated daily for EAE pathology according to the EAE evaluation criteria described above. For comparison, monophasic EAE-induced NR4A2-deficient mice (without administration) were evaluated daily for EAE pathology. OCH was administered orally as a suspension of PBS, and PBS was also administered orally.

Figure 5:
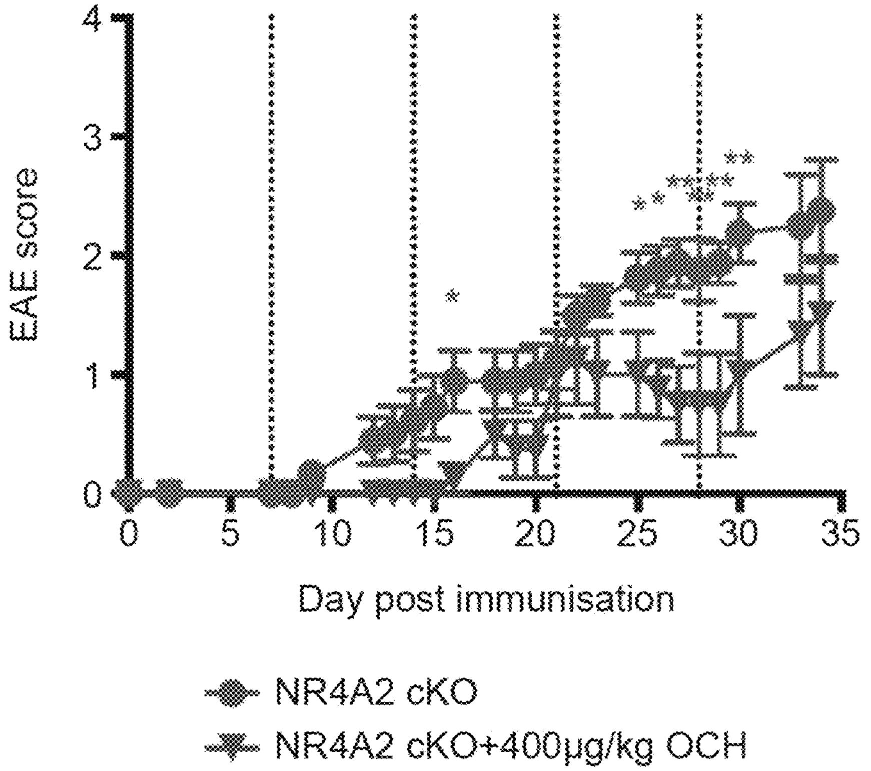
FIG. 5 is a diagram showing the EAE scores of NR4A2-deficient mice in which EAE was induced by $MOG_{35-55}$ peptide sensitization.
Figure 5:
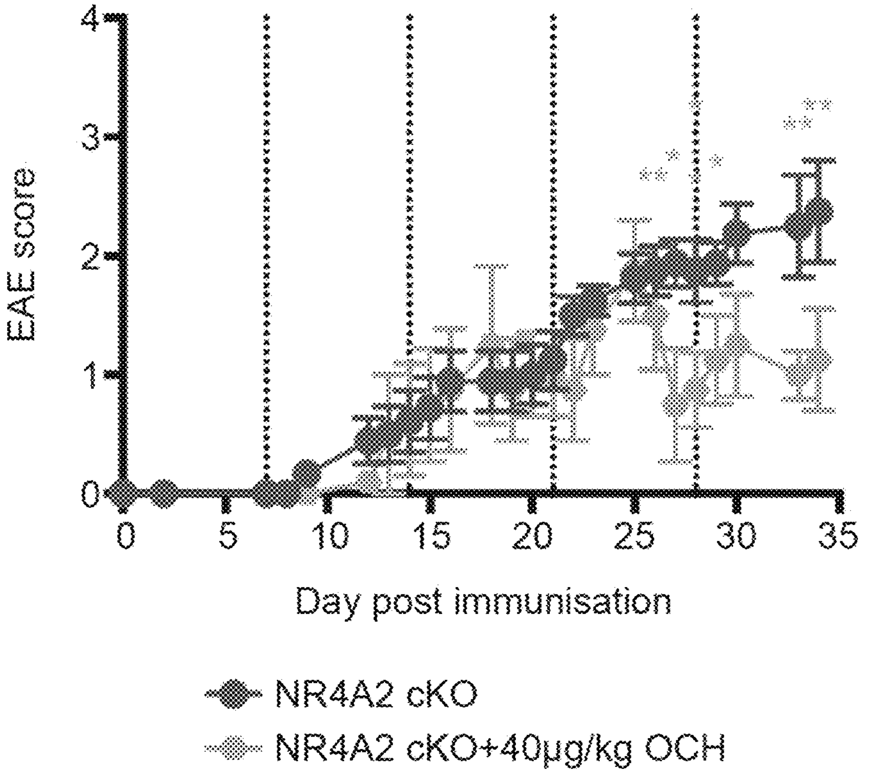

The results are shown in FIG. 5. In the EAE model of NR4A2-deficient mice, no early EAE pathology was observed, and late EAE pathology was improved in all administration groups, with more marked improvement in the high-dose administration group. OCH administration was suggested to improve the late EAE pathology in a dose-dependent manner.

(5) Effect of OCH Administration on NR4A2-Deficient Mice

NR4A2-deficient mice to which monophasic EAE was induced in the same manner as in 1. (2) described above or B6 mice (Control) received OCH at a dose of 40 μg/kg or 400 μg/kg 5 days, 10 days, 15 days, 20 days, 25 days, and 30 days after induction. 34 days after induction (Day 34), spleens were taken from mice and T cells were extracted. Changes in production of cytokines (IFNγ and IL-17) when the MOG peptide was administered to the obtained T cells at a predetermined concentration (MOG recall response) were investigated. Cytokine concentrations in culture supernatants were measured by using a typical ELISA method. No significant IL-17 was detected in NR4A2-deficient mice, confirming negligible involvement of Th17 cells in the model of EAE induced in these mice. OCH was administered orally as a suspension of PBS, and PBS was also administered orally.

Figure 6:
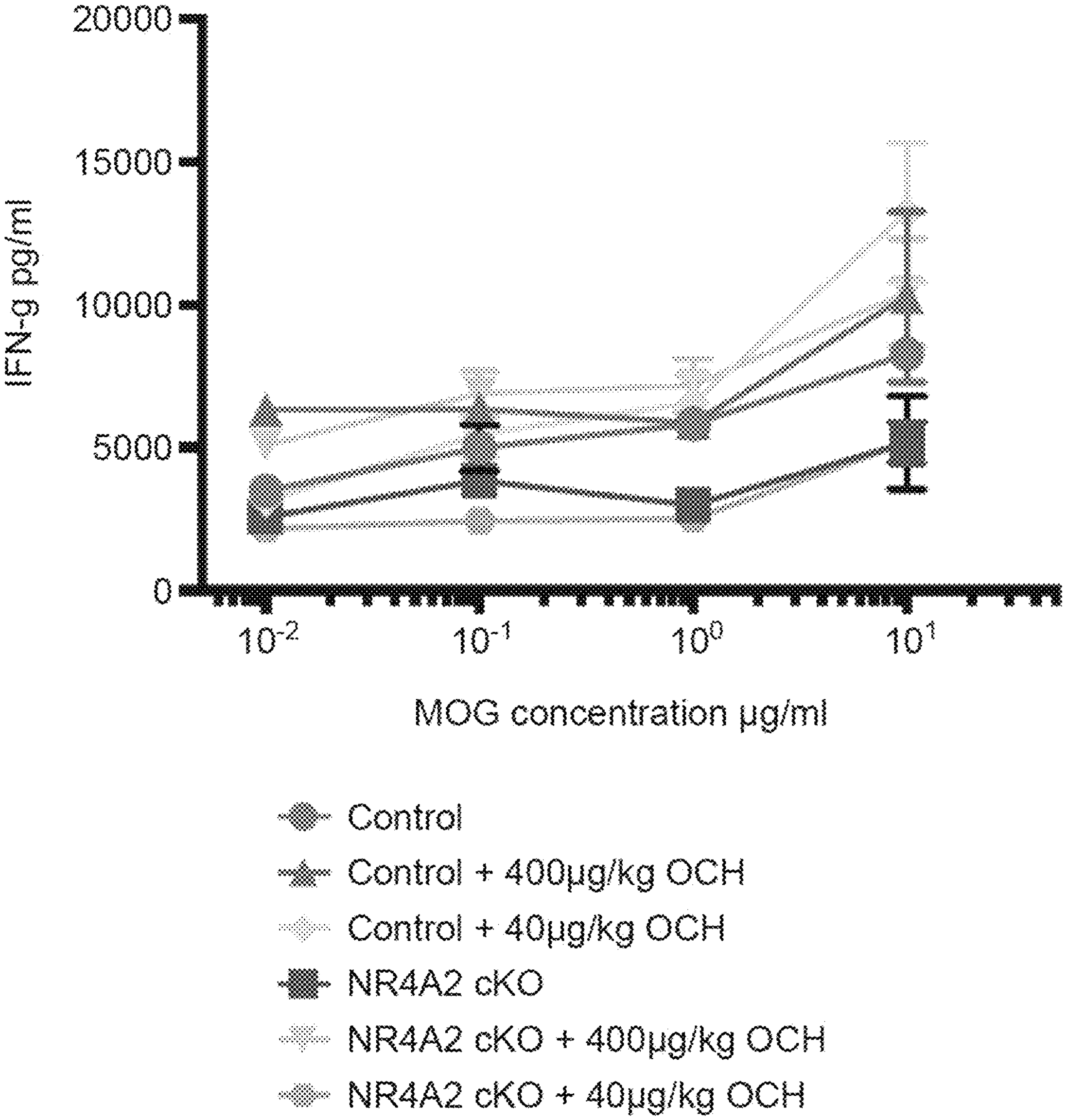
FIG. 6 is a diagram showing the amount of IFNγ produced when $MOG_{35-55}$ peptide was added to spleen-derived T cells of mice sensitized with $MOG_{35-55}$ peptide.
Figure 7:
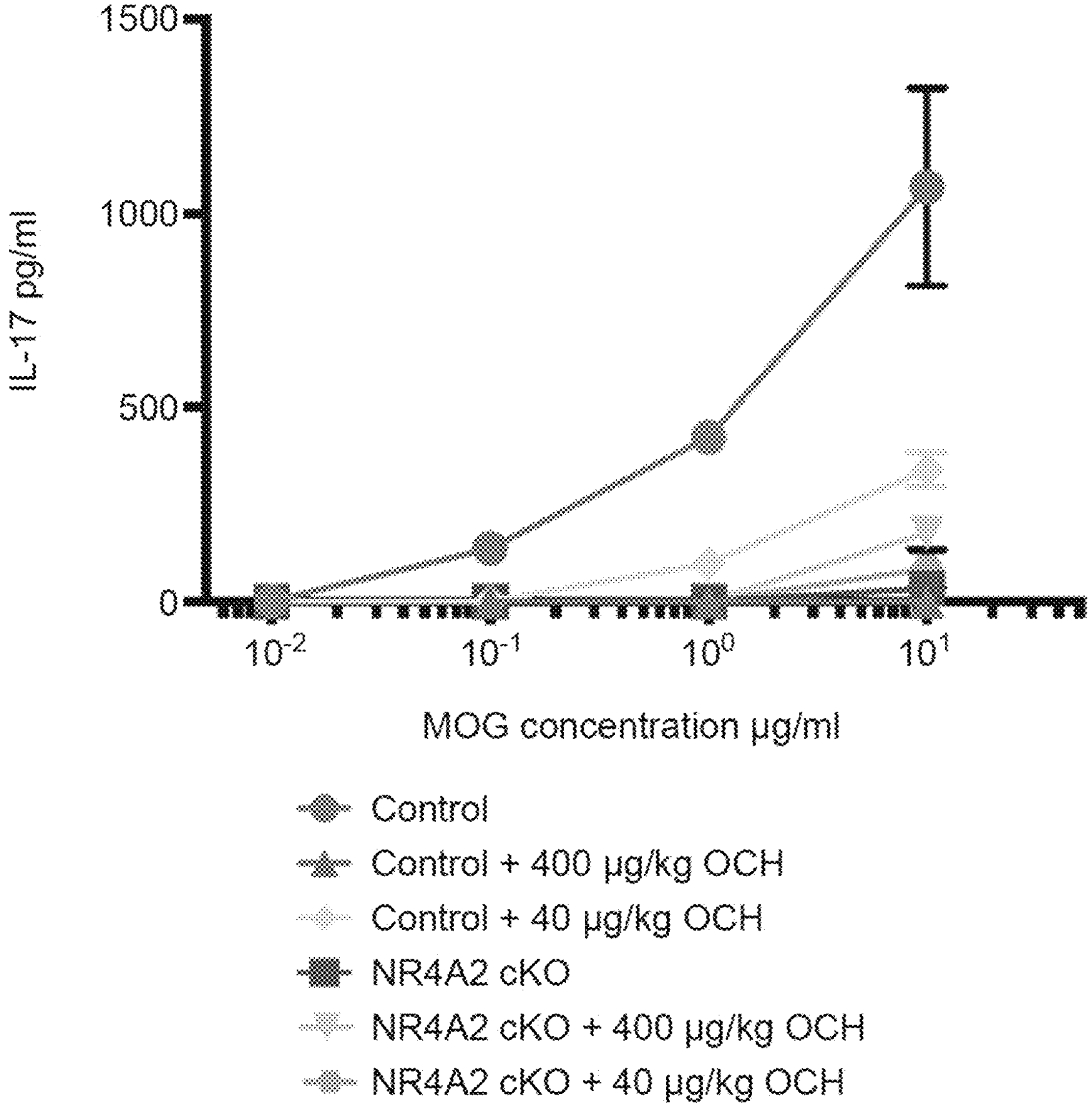
FIG. 7 is a diagram showing the amount of IL-17 produced when $MOG_{35-55}$ peptide was added to the spleen-derived T cells.

The results are shown in FIG. 6 (IFNγ) and FIG. 7 (IL-17). As shown in FIG. 6, OCH administration did not significantly affect the production of IFNγ in either B6 mice or NR4A2-deficient mice. As shown in FIG. 7, in B6 mice, the production of IL-17 was significantly increased, whereas in the OCH-administered group of B6 mice, the production of IL-17 was decreased, indicating that the activity of Th17 cells was suppressed. Meanwhile, no significant increase in IL-17 production was observed in NR4A2-deficient mice, and no significant change due to OCH administration was observed. This confirms that the Th17 cell function was significantly reduced in the same mice, and means that the improvement effect of OCH on EAE induced in NR4A2-deficient mice did not result from the suppression of Th17 cells.

The invention claimed is:

1. A method for treating a progressive disease caused by an increase in Eomes-positive CD4-positive T cells, the method comprising administering a composition comprising the compound represented by formula (I) or a salt thereof as an active ingredient:

(I)

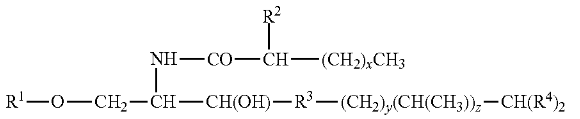

wherein R1 is an aldopyranose residue, R2 is a hydrogen atom or a hydroxy group, R3 is —CH(OH)—CH2—, R4 is a hydrogen atom or CH3, x is 11 to 35, and y and z each are an integer satisfying y+z=0 to 3, and wherein the progressive disease is progressive relapsing multiple sclerosis, primary progressive multiple sclerosis, or secondary progressive multiple sclerosis.

2. The method for treating a progressive disease according to claim 1, wherein the composition is administered orally.

3. A method for treating a progressive disease caused by an increase in Eomes-positive CD4-positive T cells, the method comprising administering a composition comprising the compound represented by (25,3S,4R)-1-O-(α-D-galactosyl)-2-(N-tetracosanoylamino)-1,3,4-nonanetriol or a salt thereof, wherein the progressive disease is progressive relapsing multiple sclerosis, primary progressive multiple sclerosis, or secondary progressive multiple sclerosis.

4. The method for treating a progressive disease according to claim 3, wherein the composition is administered orally.

5. The method according to claim 1, wherein the progressive disease is progressive relapsing multiple sclerosis.

6. The method according to claim 1, wherein the progressive disease is primary progressive multiple sclerosis.

7. The method according to claim 1, wherein the progressive disease is secondary progressive multiple sclerosis.

8. The method according to claim 3, wherein the progressive disease is progressive relapsing multiple sclerosis.

9. The method according to claim 3, wherein the progressive disease is primary progressive multiple sclerosis.

10. The method according to claim 3, wherein the progressive disease is secondary progressive multiple sclerosis.

* * * * *